United States Patent
Gualandi et al.

(10) Patent No.: US 9,433,569 B2
(45) Date of Patent: Sep. 6, 2016

(54) DENTAL CARE PRODUCTS COMPRISING CARBONATE-SUBSTITUTED FLUORO-HYDROXYAPATITE PARTICLES

(75) Inventors: Paolo Gualandi, Funo di Argelato (IT); Andrea Gualandi, Funo di Argelato (IT); Jacopo Gualandi, Funo di Argelato (IT); Ismaela Foltran, Tarzo (IT); Elisabetta Foresti, Pietrasanta (IT); Marco Lelli, Monghidoro (IT); Marco Marchetti, Montefiore dell'Aso (IT); Filippo Pierini, Bologna (IT); Norberto Roveri, Bologna (IT); Stefania Vecchiotti, Grottammare (IT); Isidoro Giorgio Lesci, Castel Bolognese (IT)

(73) Assignee: Coswell S.p.A., Funo di Argelato (BO) (IT)

(*) Notice: Subject to any disclaimer, the term of this patent is extended or adjusted under 35 U.S.C. 154(b) by 73 days.

(21) Appl. No.: 14/122,109

(22) PCT Filed: May 26, 2011

(86) PCT No.: PCT/EP2011/002606
§ 371 (c)(1),
(2), (4) Date: Nov. 25, 2013

(87) PCT Pub. No.: WO2012/159645
PCT Pub. Date: Nov. 29, 2012

(65) Prior Publication Data
US 2014/0099272 A1    Apr. 10, 2014

(51) Int. Cl.
| A61Q 11/00 | (2006.01) |
| A61K 8/21 | (2006.01) |
| A61K 8/24 | (2006.01) |
| A61K 6/00 | (2006.01) |
| A61K 33/10 | (2006.01) |
| A61K 9/14 | (2006.01) |
| A61K 8/69 | (2006.01) |
| A61K 8/27 | (2006.01) |

(52) U.S. Cl.
CPC . *A61K 8/69* (2013.01); *A61K 8/27* (2013.01); *A61Q 11/00* (2013.01); *C01P 2002/72* (2013.01); *C01P 2002/82* (2013.01); *C01P 2002/85* (2013.01); *C01P 2004/03* (2013.01); *C01P 2004/04* (2013.01)

(58) Field of Classification Search
CPC ........ A61K 8/21; A61K 33/42; A61Q 11/00; A61L 27/46
See application file for complete search history.

(56) References Cited

U.S. PATENT DOCUMENTS 4,048,300 A    9/1977 Tomlinson et al.
4,177,258 A  * 12/1979 Gaffar et al. .................. 424/52

FOREIGN PATENT DOCUMENTS

| EP | 0346957 A1 | 12/1989 |
| EP | 1762215 A1 | 3/2007 |
| RU | 2179437 C2 | 2/2002 |
| WO | WO 00/03747 A2 | 1/2000 |
| WO | WO 2007/137606 A1 | 12/2007 |

OTHER PUBLICATIONS

Uggeri et al. In vitro effects of Mg/Sr-substituted hydroxyapatite on osteoblast activity. (2010). Italian Journal of Anatomy and Embryology. vol. 115. p. 172.*
International Search Report and Written Opinion dated Aug. 22, 2012 for International Application No. PCT/EP2011/002606.
Landi E. et al.: "Development of Sr and C03 co-substituted hydroxyapatites for biomedical applications", ACTA Biomaterialia, Elsevier, Amsterdam, NL, vol. 4, No. 3, May 1, 2008, pp. 656-663.
Bigi A. et al.: "Fluoride and carbonate incorporation into hydroxyapatite under condition of cyclic pH variation", Journal of Inorganic Biochemistry, Elsevier Inc., US, vol. 27, No. 1, May 1, 1986, pp. 31-39.
Landi E. et al.: "Biomimetic Mg- and Mg, C03-substituted hydroxyapatites: synthesis characterization and in vitro behaviour", Journal of the European Ceramic Society, Elsevier Science Publishers, Barking, Essex, GB, vol. 26, No. 13, Jan. 1, 2006, pp. 2593-2601.
Cacciotti I. et al.: "Mg-substituted hydroxyapatite nanopowders: Synthesis, thermal stability and sintering behaviour", Journal of the European Ceramic Society, Elsevier Science Publishers, Barking, Essex, GB, vol. 29, No. 14, Nov. 1, 2009, pp. 2969-2978.

* cited by examiner

*Primary Examiner* — Frederick Krass
*Assistant Examiner* — Tracy Liu
(74) *Attorney, Agent, or Firm* — Husch Blackwell LLP

(57) ABSTRACT

A dental care product comprising carbonate-substituted fluoro-hydroxyapatite particles having the formula: $Ca_{(10-z-y-m)}Zn_xSr_yM_m(PO_4)_{(6-z)}(CO_3)_z(OH)_{2-w}F_w$ wherein M is selected from the group comprising Mg, Se, K and mixtures thereof; x is a number comprised between 0 and 0.02; y is a number comprised between 0.0010 and 0.015; m is a number between 0 and 0.5; z is a number comprised between 0.0010 and 0.010 and w is a number comprised between 0.000002 and 0.0001; wherein said fluoro-hydroxyapatite particles have a crystallinity degree CD comprised between 50 and 85%.

34 Claims, 5 Drawing Sheets

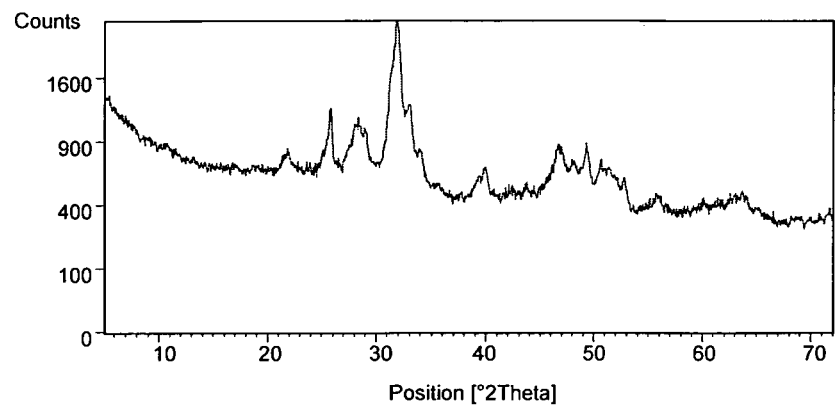
Figure 1: X Ray Diffraction of ZnCHA (comparative)
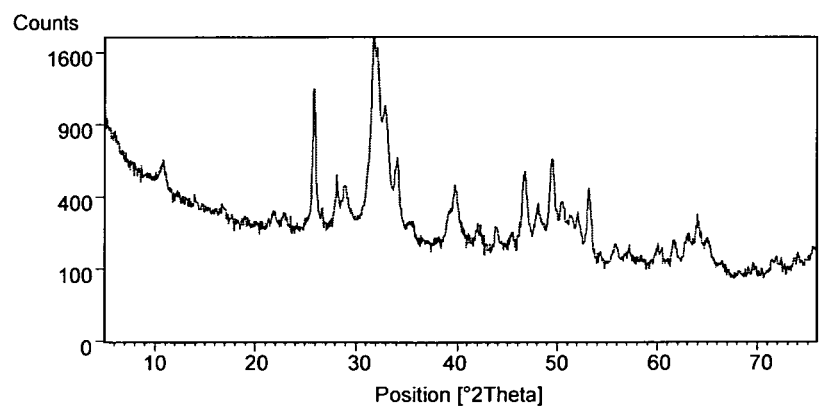
Figure 2: X Ray Diffraction of F-ZnCHA (comparative)

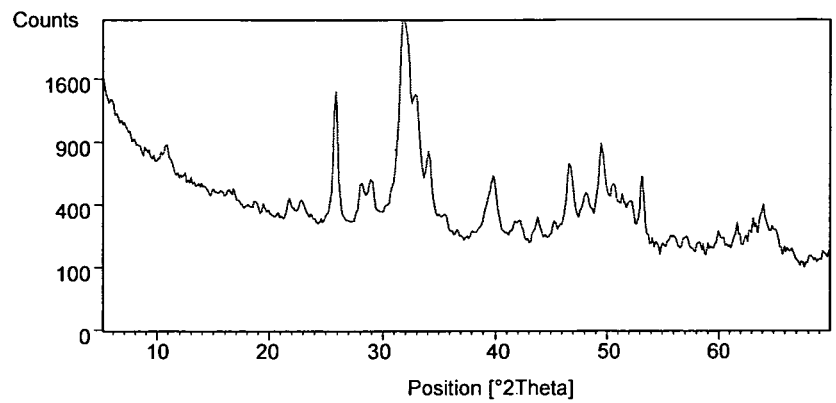
Figure 3: X Ray Diffraction of Sr-ZnCHA (comparative)
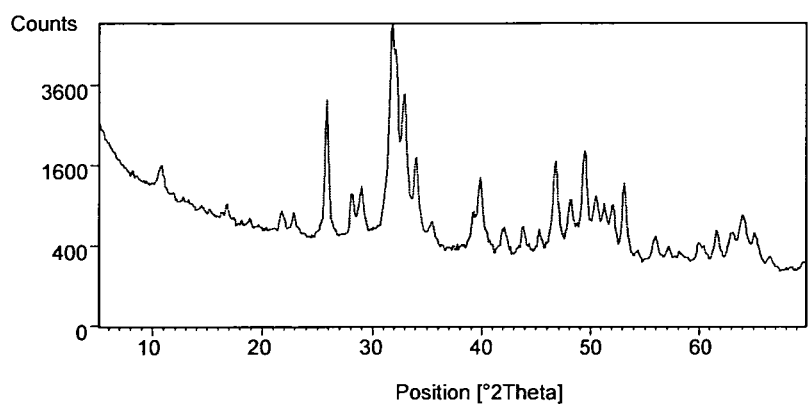
Figure 4: X Ray Diffraction of Zn,Sr,FCHA
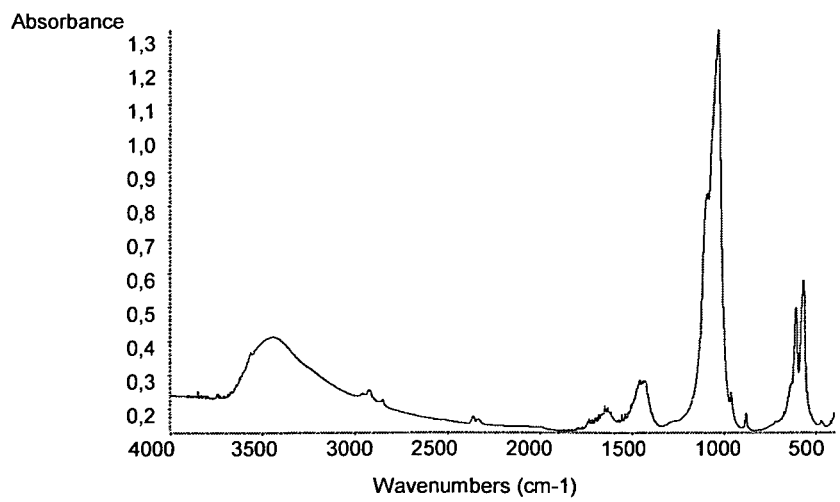
Figure 5: FT-IR Spectrum of Zn,Sr,FCHA

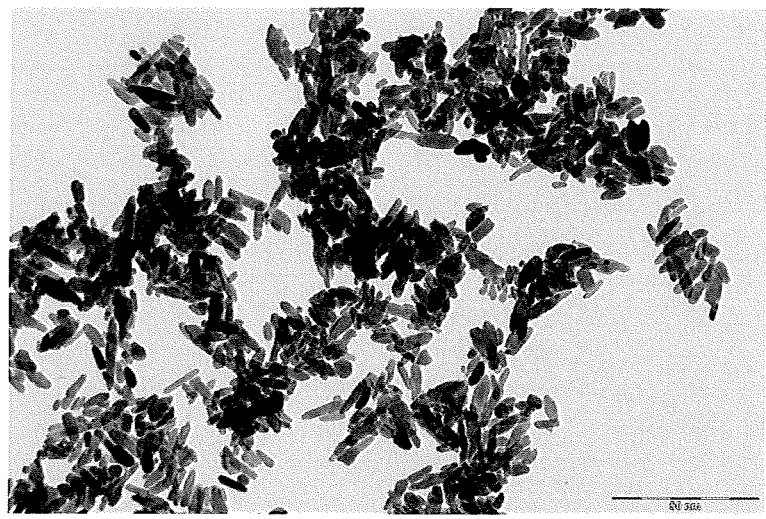
Figure 6a: SEM images of Zn,Sr,FCHA
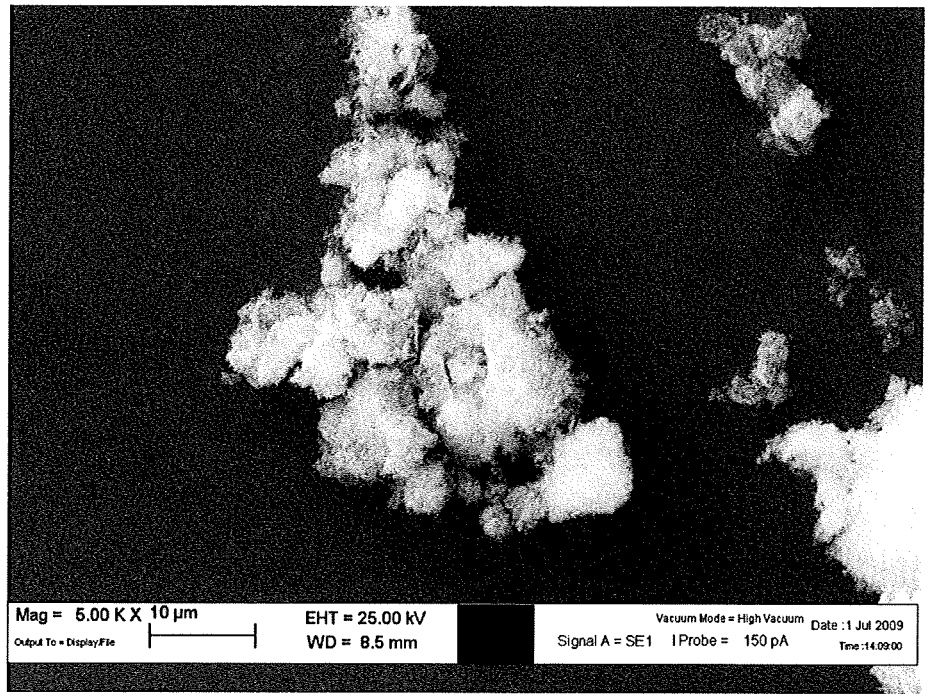
Figure 6b: TEM images of Zn,Sr,FCHA

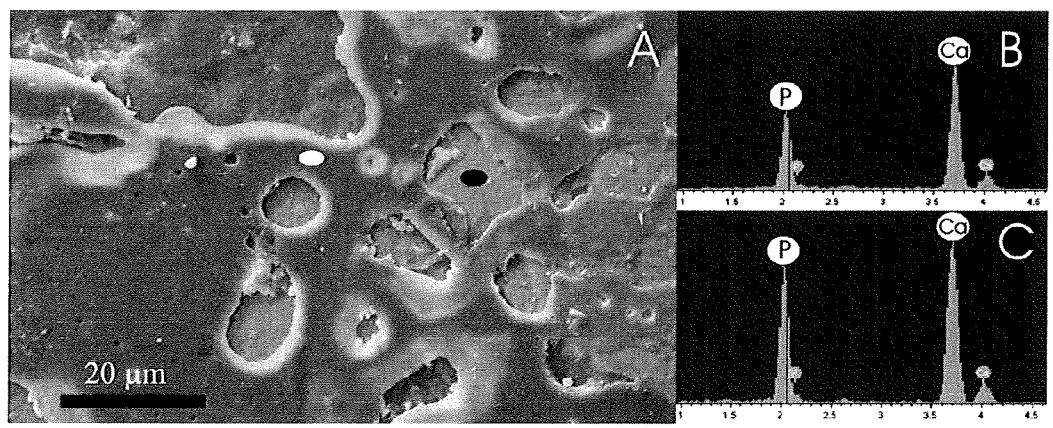
Figures 7a–7c: Respectively SEM image (7a) and EDX spectrum (7b and 7c) of enamel brushed with toothpaste containing Zn,Sr,FCHA

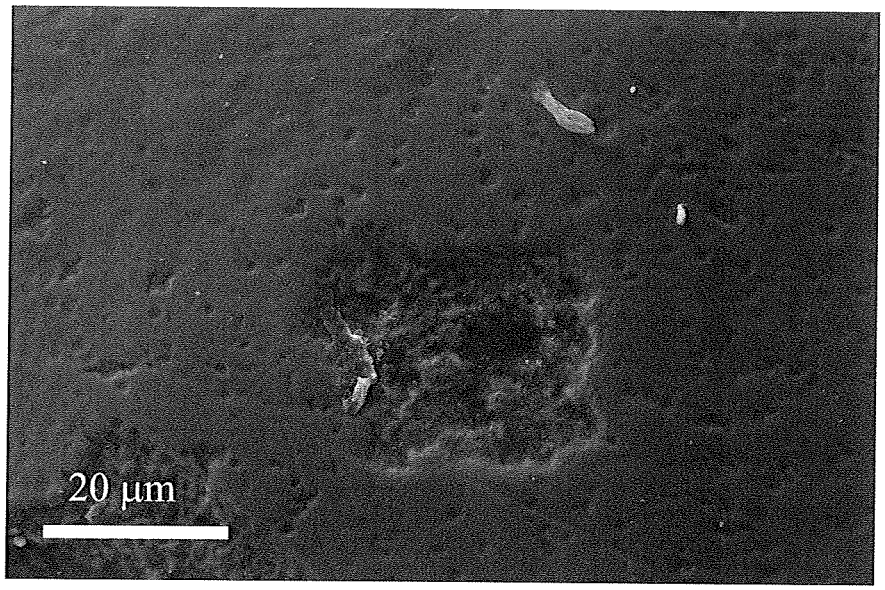
Figure 8a: SEM image of enamel brushed with common toothpaste
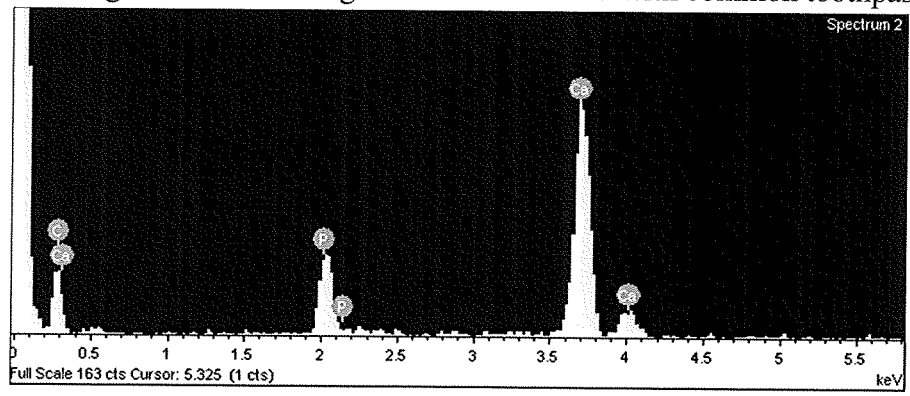
Figure 8b: EDX spectrum of enamel brushed with common toothpaste

DENTAL CARE PRODUCTS COMPRISING CARBONATE-SUBSTITUTED FLUORO-HYDROXYAPATITE PARTICLES

CROSS REFERENCE TO RELATED APPLICATIONS

This Application is a U.S. National Phase patent application of International Application PCT/EP2011/002606, filed May 26, 2011. The disclosure of International Application PCT Application No. PCT/EP2011/002606 is incorporated herein by reference.

FIELD OF THE INVENTION

The invention relates to dental care products comprising carbonate-substituted fluoro-hydroxyapatite particles and to a process for their preparation.

More specifically, the invention relates to dental care products for dental hygiene comprising carbonate-substituted fluoro-hydroxyapatite particles such as, for example, solutions, suspensions, oils, gels, pastes, dentifrices, or other solid products.

According to other aspects, the invention relates to a process for preparing a suspension for dental hygiene, to a process for manufacturing a dental care product comprising the aforementioned carbonate-substituted fluoro-hydroxyapatite particles, as well as to a method of providing at the teeth outer surface a source of $F^-$ and $Sr^{++}$ ions which may be locally released at an acidic pH by means of the carbonate-substituted fluoro-hydroxyapatite particles of the invention.

BACKGROUND OF THE INVENTION

Enamel is the hardest material in vertebrates and is the most highly mineralized skeletal tissue present in the body. Mature enamel, considered the most resistant and tough material in the biological world, is composed of carbonate hydroxyapatite (CHA) (95-97% wt) and less than 1% wt of organic material. Unlike other biomineralized tissues, such as bone and dentin, mature enamel does not contain cells and therefore cannot be regenerated itself and therefore cannot be biologically remodeled. Consequently, enamel regeneration cannot take place in vivo. There is no biological process that can repair degraded or damaged enamel, evidencing the need for synthetic enamel biocompatible materials able to repair teeth decay.

Enamel makes up the outermost layer of the tooth crown having a thickness of about 1-2 mm and containing a high mineral content which imparts to the enamel a high modulus, but also making it susceptible to cracking. Dentine lies below the enamel and is tougher, forming the bulk of the tooth and absorbing stresses from enamel, preventing its fracture.

The mechanisms involved in the damage of dental hard tissue are related to the acid attacks on the outer few micrometers of the enamel, with the consequent demineralization and dissolution of the minerals.

Frequent application of a high concentration of topical fluoride may be of some benefit in preventing further demineralization and increasing the abrasion resistance of erosion lesions. In-vitro studies have shown that inhibition of dissolution of synthetic carbonated hydroxyapatite is a logarithmic function of the fluoride concentration in solution.

Most of the products and devices commonly used to counter enamel and dentine erosion such as fluoride, work by reducing apatite dissolution and increasing surface micro hardness, but are unable to reconstruct the lost mineral.

In vitro, fluoride (0.02-0.10 mg/L) addition to a supersaturated solution of calcium phosphate induces the crystallization of hydroxyapatite, $Ca_{10}(PO_4)_6(OH)_2$ which is the mineral phase of bone and teeth. Increasing fluoride concentration fluoroapatite $Ca_{10}(PO_4)_6F_2$ is formed and appears in more ordered and bigger apatite crystals which are less soluble in an acidic environment.

In the body, in vivo fluoride is mainly associated with calcified tissue, bone and teeth due to its high affinity to calcium. Fluoride modifies the bone mineral phase by replacing the hydroxyl groups in the hydroxyapatite phase producing its partial conversion into fluoroapatite. The increased electrostatic stability and crystallinity of flouride substituted hydroxyapatite increases the bone density and hardness reducing the mechanical strength.

The use of fluoride-containing oral care products are recommended especially in countries where the fluoride concentration in drinking water is low even if there are considerable differences regarding the starting time (birth-6 months of age) and amounts related to age. Fluoride is not essential for human growth and development and its content in the body is not under physiological control. Adsorbed fluoride is rapidly distributed by circulation to the intracellular and extra cellular fluid, but is retained only in calcified tissues.

Fluoride accumulation in skeleton changes bone mechanical behaviour reducing bone strength and increasing its density and stiffness, causing skeletal deformities and risk of fractures. Fluoride is not irreversibly bound to bone and can be released during remodelling of bone.

In adults, adsorbed fluoride is only partially less than 50% retained in skeleton and the remainder excreted prevalently via the kidney. On the contrary, in infants fluoride retention in bone can be as high as 90% and appears also incorporated into dental enamel during teeth formation. Excessive intake of fluoride during enamel maturation from birth to eight years of age, when enamel formation is complete, can lead to reduced mineral phase content of enamel and to dental fluorosis of deciduous, but prevalently of permanent teeth.

For these reasons, toothpastes containing a very high fluoride concentration exceeding the International Standards Organization limits are exclusively prescribed by professionals and are not recommended for children. The European Food Safety Authority (EFSA) Scientific Panel considers that the maximum fluoride intake should be of 0.1 mg fluoride/kg/day in children aged 1-8 years which is equivalent to 1.5 and 2.5 mg fluoride per day in children aged 1-3 years and 4-8 years respectively.

RELATED ART

In recent times and based on the fact that the teeth bone tissue is primarily constituted by non-stoichiometric hydroxyapatite containing specific substituting ions at both the cationic and anionic reticular sites, the use of products comprising fluoridated hydroxyapatite has been proposed for the treatment of bone defects in the fields of reconstructive bone surgery, surgical stomatology, traumatology, orthopedics and dentistry.

Thus, for example, European Patent Application EP 1762215 discloses a toothpaste comprising rod-shaped apatite crystals such as hydroxyapatite, fluoroapatite and fluorohydroxyapatite with length-to-width ratio significantly greater than 5. U.S. Pat. No. 4,048,300 discloses a dental preparation for remineralising teeth and providing fluoride to pits and fissures of teeth with calcium and phosphate components including fluorapatite, fluorohydroxyapatite, apatite, calcium deficient apatite and hydroxyapatite.

Russian Patent Application RU 2179437, on the other hand, discloses an amorphous carbonized and fluorinated hydroxyapatite useful for manufacturing a toothpaste.

According to this reference, such a composition would be completely compatible with human body tissues, in particular with human tooth enamel.

European Patent Application EP 0346957 discloses oral compositions comprising an desensitising agent, such as potassium nitrate or strontium acetate, and a particulate abrasive material comprising hydroxyapatite. According to this reference, these compositions are suitable for treating sensitive teeth.

International Patent Application WO 00/03747 discloses nanocrystalline materials based on apatite having an average size of the crystallites comprised between 0.5 and 200 nm, particularly for use in the fields of dentistry and dental hygiene in order to induce enamel and dentine remineralisation.

More specifically, this reference discloses an apatite-based nanostructured material obtained by lattice destabilisation treatment under high energy.

International Patent Application WO 2007/137606 discloses biologically active nanoparticles of a carbonate-substituted hydroxyapatite, particularly for use in oral or dental hygiene in order to improve teeth desensitization and remineralisation.

SUMMARY OF THE INVENTION

In connection with the possible benefits associated to the use of fluoride in the preparations for dental care, the Applicant observed that the dental care products of the prior art are affected by a limit in the maximum amount of fluoride which can be incorporated therein.

As a matter of fact and as noted above, fluorides in a toothpaste, whilst well known for their anti-caries benefits, are toxic if ingested at high levels, in particular in children because of an adverse dose to weight ratio, leading to the aforementioned maximum tolerable limits of daily fluoride intake indicated by EFSA.

The Applicant has surprisingly discovered that suitable amounts of remineralizing and cariostatic elements such as fluorine and strontium may be provided in a dental care product in such a way as to avoid any possible release and subsequent ingestion from the dental care composition during use.

More particularly, the Applicant has surprisingly discovered that such an accidental release of fluoride may be avoided if the fluorine and strontium ions are chemically bonded to carbonate-substituted hydroxyapatite particles which are substantially insoluble at the normal pH conditions of the oral cavity but become soluble when the pH becomes acidic.

Accordingly, the present invention provides improved products for dental hygiene having both remineralisation and cariostatic effects, comprising carbonate-substituted fluoro-hydroxyapatite particles capable to convey, directly to the surface of the enamel, $F^-$ and $Sr^{++}$ ions only when this is necessary, i.e. when the pH of oral cavity becomes acidic, by means of a hydroxyapatite-type carrier substantially insoluble under conditions of normal pH of the oral cavity (6.3-7.3) which becomes soluble when the pH becomes acidic (pH<5) locally releasing $F^-$ and $Sr^{++}$ ions in proximity to enamel and dentine.

The Applicant has also observed that products for dental hygiene comprising said substantially insoluble hydroxyapatite-type carrier is capable of forming a thin film on the outer surface of the enamel even in the limited time available during the normal routine of dental hygiene. Said film solubilizes when the pH of the oral cavity becomes acidic locally releasing fluorine and strontium ions, only when this is necessary, effectively improving teeth remineralisation and showing a cariostatic effect.

The Applicant has also surprisingly and unexpectedly found a synergistic effect of fluorine and strontium ions when these are inserted in the carrier of hydroxyapatite effectively improving the enamel crystallinity i.e. improving teeth remineralisation.

Dental care products comprising carbonate-substituted fluoro-hydroxyapatite particles according to the invention are defined in attached claim 1.

More specifically, the carbonate-substituted fluoro-hydroxyapatite particles of the invention have the formula:

$$Ca_{(10-x-y-m)}Zn_xSr_yM_m(PO_4)_{(6-z)}(CO_3)_z(OH)_{2-w}F_w$$

wherein M is selected from the group comprising Mg, Se, K and mixtures thereof; x is a number comprised between 0 and 0.02; y is a number comprised between 0.0010 and 0.015; m is a number between 0 and 0.5; z is a number comprised between 0.0010 and 0.010 and w is a number comprised between 0.000002 and 0.0001; and wherein said fluoro-hydroxyapatite particles have a crystallinity degree CD comprised between 50 and 85%.

The crystallinity degree being defined as

$$CD=(1-X/Y) \bullet 100$$

wherein:
Y=height of the diffraction maximum at 2θ=33°,
X=height of the diffraction background at 2θ=33° of the particles X-ray diffraction pattern.

For the purposes of the present description and of the claims which follow, the expression: particles, is intended to indicate nanoparticles or microparticles.

When particles ere considered of nanometric size, their dimension range from few nanometers up to some hundreds of nanometers, but for biomedical applications the dimension range is usually reduced from 10 nm to 100 nm because only nanoparticles of these dimensions can go across the cellular membrane. In order to avoid any possible consequence related to the presence of nanoparticles inside the cells it is preferred to use nanoparticles larger than 100 nm for biomedical applications which do not require an intracellular action. On the other hand nanoparticles aggregated in a cluster can realize particles of micrometric dimension.

For the purposes of the present description and of the claims which follow, the term nanoparticle, is used to indicate a particle having a size generally below 0.1 µm, preferably between 0.01 µm and 0.1 µm.

For the purposes of the present description and of the claims which follow, the term microparticle, is used to indicate aggregates or "clusters" of inorganic nanoparticles mentioned above and having a size comprised between 0.2 µm and 10 µm, preferably between 0.5 µm and 2 µm.

Single nanoparticles can have quite different morphology, but preferably, the nanoparticles of the invention have a flattened acicular shape mimicking the morphology of bone hydroxyapatite nanoparticles. The Applicant considers the nanoparticles biomimetic morphology the most adapted to interact with the dentine and enamel surface.

For the purposes of the present description and of the claims which follow, the expression: crystallinity degree, is intended to indicate the percentage of the hydroxyapatite compound present in the crystalline state.

For the purposes of the invention, the crystallinity degree can be measured according to known methods, such as, for example, by using x-ray diffraction analysis.

Within the framework of the definition given above, the crystallinity degree CD is measured according to the method described in: Landi, E., Tampieri, A., Celotti, G., Sprio, S., "*Densification behaviour and mechanisms of synthetic hydroxyapatites*", *J. Eur. Ceram. Soc.*, 2000, 20, 2377-2387 (hereinafter in short: the Landi et al. method).

For the purposes of the present description and of the claims which follow, the expression: lower than, as used before any numerical value, is meant to exclude such a numerical value and used to encompass only a range of lower values.

For the purposes of the present description and of the claims which follow, except where otherwise indicated, all numerical values expressing parameters such as amounts, weights, temperatures, percentages, and so forth, are to be understood as being modified in all instances by the term "about". Also, all ranges include any combination of the maximum and minimum points disclosed and include any intermediate ranges therein, which may or may not be specifically enumerated herein.

According to a preferred embodiment of the invention, the particles can further comprise an effective amount of zinc ions.

Advantageously, the aforementioned ions effectively exploit an antibacterial activity capable of preventing generation of carious tooth and periodontal diseases such as alveolar blennorrhoea and reducing halitosis phenomena. In this preferred embodiment, therefore, the dental composition of the invention is also advantageously capable of effectively exploiting an antibacterial effect and, accordingly, effectively treating teeth and gums disorders and in general increasing oral hygiene even in the limited time available during the normal routine of dental hygiene.

As mentioned above, the particles of the invention are carbonate-substituted fluoro-hydroxyapatite particles which incorporate carbonate ions in the apatite structure. This feature advantageously enhances the biological activity of the particles of the invention, since the carbonate ion is also found in the structure of natural hydroxyapatite. In this regard, it is to be observed that the carbonate ion can occupy in two different sites in the natural hydroxyapatite structure: namely, it can partially substitute the OH-ion (site A) and/or the $PO_4^{3-}$ ion (site B). Both the total carbonate content (in the range of 3-8 wt. %) and the relative quantities of type A and type B carbonation (A/B in the range of 0.7-0.9) found in the natural carbonate-substituted hydroxyapatite depend on the age of the individual and on the biological localization of the calcified tissue.

In a preferred embodiment of the invention, the carbonation preferably takes place at site B.

In a preferred embodiment of the invention, the hydroxyapatite particles comprise from 1 to 15% by weight and, more preferably, from 1 to 10% by weight based on the total weight of the particles of carbonate substituted into the hydroxyapatite structure.

In this way, the biological activity of the particles of the invention is advantageously enhanced, since their structure more closely resembles the structure of the natural apatite present in the teeth tissues.

According to a preferred embodiment of the invention, the ratio A/B between the carbonate substitution at the hydroxyl site (A) and the carbonate substitution at the phosphate site (B) of the hydroxyapatite is comprised between 0.05 and 0.5 and, still more preferably, comprised between 0.18 and 0.33.

According to another preferred embodiment of the invention, the carbonate substitution at the phosphate site (B) of the hydroxyapatite is greater than or equal to 65% by weight and, still more preferably, comprised between 90% and 100% by weight, of the total carbonate present in the hydroxyapatite.

These preferred patterns of carbonate substitution in the hydroxyapatite structure advantageously allow to increase the solubility of the particles in a biological environment. Additionally, the carbonate substitution at the phosphate site (B) advantageously induces a higher affinity of the hydroxyapatite particles for the osteoblast cell, increasing cellular adhesion and collagen production.

In one preferred embodiment, the dental care product of the invention comprises carbonate-substituted fluoro-hydroxyapatite particles having the formula

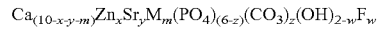

$$Ca_{(10-x-y-m)}Zn_xSr_yM_m(PO_4)_{(6-z)}(CO_3)_z(OH)_{2-w}F_w$$

wherein M is Mg, x, y, z and w are as described above and m is a number between 0.01 and 0.5; and wherein said fluoro-hydroxyapatite particles have a crystallinity degree CD comprised between 55 and 80%.

In one preferred embodiment, the dental care product of the invention comprises carbonate-substituted fluoro-hydroxyapatite particles having the formula

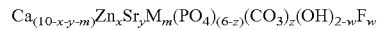

$$Ca_{(10-x-y-m)}Zn_xSr_yM_m(PO_4)_{(6-z)}(CO_3)_z(OH)_{2-w}F_w$$

wherein M is $Mg_{m1}Se_{m2}$ wherein $m_1$ is a number between 0.01 and 0.5, $m_2$ is a number between 0.001 and 0.5 and $m_1+m_2 \leq 0.5$, x, y, z and w are as described above; and wherein said fluoro-hydroxyapatite particles have a crystallinity degree CD comprised between 60 and 75%.

In one preferred embodiment, the dental care product of the invention comprises carbonate-substituted fluoro-hydroxyapatite particles having the formula

$$Ca_{(10-x-y-m)}Zn_xSr_yM_m(PO_4)_{(6-z)}(CO_3)_z(OH)_{2-w}F_w$$

wherein M is $Mg_{m1}Se_{m2}K_{m3}$ wherein $m_1$ is a number between 0.01 and 0.5, $m_2$ is a number between 0.001 and 0.5, $m_3$ is a number between 0.0005 and 0.5 and $m_1+m_2+m_3 \leq 0.5$, x, y, z and w are as described above; and wherein said fluoro-hydroxyapatite particles have a crystallinity degree CD comprised between 60 and 80%.

Preferably, the dental care product including the particles of the invention may be in any physical form suitable for oral hygiene such as suspension, oil, gel or other solid product.

According to a preferred embodiment of the invention, the dental care product is in the form of a suspension including from 1% to 40% by weight, more preferably from 10% to 20% by weight, of carbonate-substituted fluoro-hydroxyapatite particles.

In a preferred embodiment of the invention, the suspension has pH comprised between 6 and 12.

In this way, the suspension may be advantageously directly used as such or mixed with other ingredients in the formulation of effective dental care products.

Most advantageously, this suspension may be produced by means of a quite simple and economic method, as will be described in more detail hereinbelow, and may be directly used, for example as a gargle or mouthwash, to treat the teeth and gums or may be mixed with other ingredients when formulating a solid or liquid product such as a toothpaste or a mouthwash.

In either case and in a preferred embodiment, it has proved advantageous to add suitable preserving agents, such as parabens or other orally acceptable preservatives known to those in the art, in order to prolong the shelf-life of the suspension and avoid the possibility of mold or bacterial contamination.

The inventors have surprisingly observed that the suspension of the invention is stable for an extended period of time even if no stabilizing agents are added thereto.

In particular, it has been observed that the suspension of the invention is stable for at least 30 days and, more generally, for about two-three months, without using any stabilizing agent.

According to a preferred embodiment of the invention, the dental care product is selected from the group consisting of: toothpaste, tooth powder, chewing gum for oral and dental hygiene, ointment for the gums, mouthwash and mouth bath concentrate and gargle.

The dental care products of this invention will, of course, also preferably contain other ingredients commonly used and known in the art to formulate such products, depending on the form of the oral product.

For instance, in the case of an oral product in the form of a dentifrice cream or paste, the product will preferably comprise a particulate abrasive agent, a humectant-containing liquid phase and a binder or thickener which acts to maintain the abrasive agent in stable suspension in the liquid phase. A surfactant and a flavoring agent are also usual preferred ingredients of commercially acceptable dentifrices.

For the purposes of the invention, a suitable particulate abrasive agent is preferably selected from the group comprising: silica, alumina, hydrated alumina, calcium carbonate, anhydrous dicalcium phosphate, dicalcium phosphate dihydrate and water-insoluble sodium metaphosphate. The amount of particulate abrasive agent will generally range from 0.5% to 40% by weight of the toothpaste.

Humectants of preferred use are glycerol and sorbitol syrup (usually comprising an approximately 70% solution). However, other humectants are known to those in the art including propylene glycol, lactitol, and hydrogenated corn syrup. The amount of humectant will generally range from 10% to 85% by weight of the toothpaste. The liquid phase can be aqueous or nonaqueous.

Likewise, numerous binding or thickening agents have been indicated for use in dentifrices, preferred ones being sodium carboxymethylcellulose and xanthan gum. Others include natural gum binders such as gum tragacanth, gum karaya and gum arabic, alginates and carrageenans. Silica thickening agents include the silica aerogels and various precipitated silicas. Mixtures of binders may be used. The amount of binder included in a dentifrice is generally between 0.1% and 5% by weight.

It is usual and preferred to include a surfactant in a dentifrice and again the literature discloses a wide variety of suitable materials. Surfactants which have found wide use in practice are sodium lauryl sulfate and sodium lauroylsarcosinate. Other anionic surfactants may be used as well as other types such cationic, amphoteric and non-ionic surfactants. Surfactants are usually present in an amount comprised between 0.5% and 5% by weight of the dentifrice.

Flavors of possible use are those usually used in dentifrices, for example those based on oils of spearmint and peppermint. Examples of other flavoring materials which may be used are menthol, clove, wintergreen, eucalyptus and aniseed. An amount comprised between 0.1% and 5% by weight is a suitable amount of flavor to incorporate in a dentifrice.

The dental care products of the invention may include a wide variety of other optional ingredients.

In the case of an oral product in the form of a toothpaste, these optional ingredients may include an anti-plaque agent such as moss extract, an anti-tartar ingredient, such as a condensed phosphate, e.g. an alkali metal pyrophosphate, hexametaphosphate or polyphosphate; a sweetening agent, such as saccharine and salts thereof; an opacifying agent, such as titanium dioxide; a preservative, such as formalin; a coloring agent; a pH controlling agent, such as an acid, base or buffer, such as citric acid. Suitable amounts of these optional ingredients may be easily selectable by those skilled in the art as a function of the specific characteristics to be imparted to the toothpaste.

In the case of an oral product in the form of a chewing gum, the composition will comprise in addition to the ingredients mentioned above a suitable gum base which may be easily selectable by those skilled in the art.

In the case of an oral product in the form of a mouthwash or gargle, the composition will comprise suitable ingredients in liquid or soluble form easily selectable by those skilled in the art, such as sorbitol, glycerol, oils and flavoring materials, solubilizing agents such as hydrogenated and ethoxylated ricin oil, surfactants, such as sodium lauryl sulfate and sodium lauroylsarcosinate, preserving agents, viscosity regulators and other suitable ingredients which may be easily selectable by those skilled in the art.

For a fuller discussion of the formulation of oral compositions reference is made to Harry's Cosmeticology, Seventh Edition, 1982, Edited by J. B. Wilkinson and R. J. Moore.

According to another aspect thereof, the present invention relates to dental care compositions comprising the aforementioned carbonate-substituted fluoro-hydroxyapatite particles.

According to another aspect thereof, the present invention relates to the aforementioned carbonate-substituted fluoro-hydroxyapatite particles.

According to another aspect thereof, the present invention relates to an improved process for manufacturing a dental care product comprising carbonate-substituted fluoro-hydroxyapatite particles which requires low investment and operating costs.

A first process for manufacturing a dental care product selected from the group consisting of: toothpaste, tooth powder, chewing gum, ointment for the gums, mouthwash and mouth bath concentrate and gargle, according to the invention is defined in attached claim 11 and comprises the steps of:

a) providing an aqueous suspension including particles as herein described; and b) mixing said aqueous suspension with other ingredients of the dental care product.

As already noted above, this process advantageously allows to readily incorporate the particles in the dental care product in a quite simple and convenient manner exploiting the useful properties, in particular stability and pH characteristics, of the suspension of particles produced in accordance with the invention.

Quite advantageously, the process for manufacturing a dental care product of the invention does not require any separation or drying of the particles, with a notable reduction of the manufacturing plant complexity, of the related investment and operating costs, of product losses during the manufacture and of production rejects.

In addition, the mixing step of the aqueous suspension of particles with other ingredients of the dental care product may be carried out with a better temperature control since the aqueous suspension reduces the friction and helps in removing the heat generated in the mixing apparatus.

An alternative second process for manufacturing a dental care product selected from the group consisting of: toothpaste, tooth powder, chewing gum, ointment for the gums, mouthwash and mouth bath concentrate and gargle, according to the invention is defined in attached claim 12 and comprises the steps of:

a') providing solid particles as herein described; and
b') mixing the solid particles with other ingredients of the dental care product.

This alternative process allows to manufacture a dental care product in all those instances in which the use of the above-described suspension of particles may not be desirable for logistic or other reasons.

According to a preferred embodiment of the invention, the aforementioned step a) comprises the steps of:

$a_1$) preparing an aqueous solution or suspension comprising a Ca compound, Ca carbonate and optionally a F compound;

$b_1$) adding Sr and optionally Zn and/or a metal M compound selected from Mg, Se, K and mixtures thereof to the aqueous solution or suspension of step $a_1$);

$c_1$) preparing a mixture of phosphoric acid and optionally a F compound;

$d_1$) forming an aqueous suspension of solid particles of a carbonate-substituted fluoro-hydroxyapatite by adding said mixture to the aqueous solution or suspension of step $b_1$), provided that at least one F compound is present in the mixture of step $c_1$) and/or in the aqueous solution or suspension of step $b_1$), while simultaneously agitating the same over a time comprised between 30 minutes and 7 hours while maintaining said solution or suspension at a temperature comprised between 10 and 90° C.; and $e_1$) agitating a suspension of particles obtained from step $d_1$) over a time comprised between 1 and 48 hours at a temperature comprised between 10° C. and 90° C.

Most advantageously, these steps allow to prepare in a fairly quick and economical way a suspension of carbonate-substituted fluoro-hydroxyapatite particles which may be readily used as such as a composition for oral hygiene or used in admixture with other ingredients to yield dental care products for oral hygiene.

Most advantageously, furthermore, these steps allow to prepare a suspension of carbonate-substituted fluoro-hydroxyapatite particles which is stable for an extended period of time even if no stabilizing agents are added thereto.

As indicated above, it has been observed that the suspension thus prepared is stable for at least 30 days and, more generally, for about two-three months, without using any stabilizing agent.

In this preferred embodiment, step $d_1$) is preferably carried out in order to achieve an aqueous suspension having a pH comprised between 5 and 13.

For the purposes of the invention, the aforementioned step $a_1$) of preparing an aqueous solution or suspension comprising a Ca compound may be carried out in any conventional manner, such as by dissolving or suspending the Ca compound in water.

According to a preferred embodiment of the invention, the Ca compound is a calcium salt selected from the group comprising: calcium hydroxide, calcium carbonate, calcium acetate, calcium oxalate, calcium nitrate, and mixtures thereof.

In this way, the cost of the process may advantageously be reduced since these Ca compounds are commodities readily available from the marked at a very low cost.

Additionally, these Ca compounds are easily workable and stockable to the advantage of the manufacturing operations.

According to a preferred embodiment of the invention, the aforementioned Zn compound is a zinc salt selected from the group comprising: zinc carbonate, zinc oxide, and zinc hydroxide, zinc acetate, zinc nitrate, and mixtures thereof.

According to a preferred embodiment of the invention, the aforementioned F compound is a fluoride salt selected from the group comprising: sodium fluoride, sodium fluoride phosphate, fluoridric acid, and mixtures thereof.

According to a preferred embodiment of the invention, the aforementioned Sr compound is a strontium salt selected from the group comprising: strontium carbonate, strontium oxide, and strontium hydroxide, and mixtures thereof.

According to a preferred embodiment of the invention, the aforementioned M compound is a metal salt selected from the group consisting of Mg compound, Se compound, K compound and mixtures thereof.

According to a preferred embodiment of the invention, the aforementioned Mg compound is a magnesium salt selected from the group comprising: magnesium carbonate, magnesium oxide, and magnesium hydroxide, magnesium acetate, and mixtures thereof.

According to a preferred embodiment of the invention, the aforementioned Se compound is a selenium salt selected from the group comprising: selenium dioxide, selenium trioxide, selenious acid, selenic acid, and mixtures thereof.

According to a preferred embodiment of the invention, the aforementioned K compound is a potassium salt selected from the group comprising: potassium carbonate, potassium oxide, potassium hydroxide, potassium nitrate, potassium hydrogen carbonate, potassium acetate, and mixtures thereof.

In a preferred embodiment, the carbonate-substituted fluoro-hydroxyapatite particles are formed in step $c_1$) by adding $PO_4^{3-}$ and optionally $F^-$ ions to the aqueous solution or suspension of step $a_1$) and $b_1$) and by simultaneously agitating this solution or suspension in order to capture the carbon dioxide present in the atmosphere and achieve the desired carbonate substitution at the phosphate site (B) of the hydroxyapatite compound being formed.

In this way, the carbonate substitution may be advantageously carried out by simply agitating the solution or suspension for example by means of a mechanical stirrer.

In an alternative embodiment, the required agitation of the solution or suspension may be achieved by bubbling air, a $CO_2^-$ containing gas or a mixture thereof into the liquid phase or by combining a mechanical stirring with a gas bubbling.

According to a preferred embodiment of the invention, step $c_1$) is carried out by adding, preferably dropwise, an aqueous solution including $PO_4^{3-}$ and optionally $F^-$ ions to the aqueous solution or suspension of step $a_1$) and $b_1$).

According to an alternative preferred embodiment of the invention, the aqueous solution including $PO_4^{3-}$ and optionally $F^-$ ions added in step $c_1$) may further comprise $HCO_3^-$ ions.

In this way, it may be possible to adjust to the proper extent the desired carbonate substitution at the phosphate site (B) of the hydroxyapatite compound being formed.

Within the framework of this preferred embodiment, the aforementioned aqueous solution including $HCO_3^-$, $PO_4^{3-}$ and optionally $F^-$ ions may be prepared by bubbling air, $CO_2$ or a mixture thereof through water to obtain a solution of carbonic acid and then adding $H_3PO_4$ and F compound thereto.

According to another alternative preferred embodiment of the invention, step $c_1$) may be carried out by simultaneously adding a first solution containing $CO_3^{2-}$ ions and a second solution containing $PO_4^{3-}$ and optionally $F^-$ ions to the aqueous solution or suspension of step $a_1$) and $b_1$).

According to a preferred embodiment of the invention, the aforementioned step a') comprises the steps of:
- $a_2$) preparing an aqueous suspension of carbonate-substituted fluoro-hydroxyapatite solid particles by means of the aforementioned step a);
- $b_2$) separating the solid particles from the suspension obtained from step $a_2$);
- $c_2$) drying the wet solid particles thus obtained.

In a preferred embodiment, the separation step $b_2$) is carried out by decantation, centrifugation or filtration using apparatuses and techniques well known to those skilled in the art.

In a preferred embodiment, the drying step $c_2$) is carried out by freezing the wet solid particles at a temperature lower than 0° C. until reaching a constant weight.

Within the framework of this preferred embodiment, the drying step $c_2$) is preferably carried out by freeze-drying the wet solid particles at a temperature comprised between $-20°$ and $-50°$ C., most preferably at about $-40°$ C.

In a preferred embodiment, the process may also comprise the additional step $d_2$) of washing the separated solid particles with water or a basic solution prior to effecting the drying step $c_2$).

Advantageously, this additional washing step $d_2$) serves the useful function of removing any acid residues possibly absorbed or trapped by the particles.

In a preferred embodiment of the dental care product manufacturing processes described above, the mixing step b) and b') is carried out in a mixing apparatus maintained under a predetermined vacuum degree, easily selectable by those skilled in the art in order to obtain a uniform mixture of ingredients, reached by using conventional vacuum pumps.

In a preferred embodiment of the first manufacturing process, the mixing step b) is carried out by
- $b^1$) mixing the aqueous suspension of step a) with other ingredients of the toothpaste except for any surfactant;
- $b^2$) incorporating at least one surfactant into the mixture thus obtained.

In this way, the formation of foam during the mixing operation may be minimized.

Within the framework of this embodiment, the incorporation step $b^2$) is preferably carried out under vacuum using a conventional equipment in order to minimize the undesired formation of foam.

According to another aspect thereof, the present invention relates to a method of providing at a teeth outer surface a source of $F^-$ and $Sr^{++}$ ions which may be locally released at an acidic pH by means of hydroxyapatite-type carrier particles, the method comprising contacting the teeth with a composition as described herein so as to form on the teeth outer surface a film including said carbonate-substituted fluoro-hydroxyapatite particles.

Most advantageously and thanks to the characteristics of the carbonate-substituted fluoro-hydroxyapatite particles described above, such a method allows to effectively remineralise the teeth, improving the enamel crystallinity, even in the limited time available during the normal routine of dental hygiene.

The contacting step may be carried out in a number of ways depending upon the dental care product. For example, if the dental care product is a toothpaste, the contacting step may be simply carried out by washing the teeth, while if the dental care product is a mouthwash, the contacting step is carried out by maintaining the mouthwash in the oral cavity for a suitable time, for example few minutes.

According to the invention and as will be shown in greater detail below, the carbonate-substituted fluoro-hydroxyapatite particles of the invention have a double effect on tooth surface.

Firstly, the dental care products of the invention are advantageously capable of restoring the enamel surface because the particles of the invention bind to the enamel surfaces, mimicking the natural bone hydroxyapatite, at any erosion area due for example, to the acid foods and drinks.

Secondly, the dental care products of the invention comprising both fluoride and strontium ions into the structure of hydroxyapatite, advantageously form a thin biomimetic coating on the outer surface of the enamel even during the usual tooth brushing. After the formation of this biomimetic coating, the plaque, the acid food and drink partially dissolve this coating, releasing strontium and fluoride ions that only in this moment are free in the mouth and are present in the physiologic percentage in which these ions are present in the tooth hydroxyapatite. Said free ions are capable of binding with the tooth hydroxyapatite forming in situ a fluoride-strontium hydroxyapatite.

According to the invention and as will be shown in greater detail below, said fluoride-strontium hydroxyapatite presents a greater degree of crystallinity with respect to the enamel hydroxyapatite. In this way, this hydroxyapatite, having higher degree of crystallinity, is more resistant to the plaque formation and to the action of food and acid drinks.

In a preferred embodiment, moreover, the dissolution of the hydroxyapatite biomimetic coating in acid conditions, may determine the release of zinc ions, known for their antibacterial properties in the mouth environment, if these ions are present in the particles formulation.

According to a preferred embodiment thereof, the present invention also provides a dental care product comprising zinc carbonate-substituted fluoro-hydroxyapatite particles capable of effectively exploiting also an antibacterial effect and, accordingly, effectively treating teeth and gums disorders and in general increasing oral hygiene even in the limited time available during the normal routine of dental hygiene.

BRIEF DESCRIPTION OF THE DRAWINGS

Additional features and advantages of the present invention will be more readily apparent by the following Examples of some preferred embodiments of the various aspects of the present invention given hereinbelow by way of illustration and not of limitation, which aspects will be better understood with reference to the attached drawings.

In these drawings:

FIG. 1 shows an X-Ray diffraction pattern of comparative zinc carbonate-substituted hydroxyapatite particles (Zn—CHA), without fluoride and strontium substitution, which displays a cristallinity degree CD of 60%;

FIG. 2 shows an X-Ray diffraction pattern of comparative zinc carbonate-substituted fluoro-hydroxyapatite particles (F—ZnCHA), with molar % of fluoride substitution comprised between 0.000002 and 0.0001), without strontium substitution, which displays a cristallinity degree CD of 63%;

FIG. 3 shows an X-Ray diffraction pattern of comparative zinc, strontium carbonate-substituted hydroxyapatite particles (Sr—ZnCHA), with molar % of strontium substitution comprised between 0.0010 and 0.015), without fluoride substitution, which displays a cristallinity degree CD of 61%;

FIG. 4 shows an X-Ray diffraction pattern of one example of zinc, strontium carbonate-substituted fluoro-hydroxyapatite particles (Zn,Sr,FCHA), with the aforementioned molar % of strontium and fluoride) according to the invention (Example 4) which displays a cristallinity degree CD of 68%;

FIG. 5 shows a FTIR spectrum of one example of carbonate-substituted fluoro-hydroxyapatite particles according to the invention which display an apatitic phase;

FIGS. 6a and 6b show TEM and SEM images of some examples of carbonate-substituted fluoro-hydroxyapatite particles according to the invention which display the micrometric size and a lamellar and acicular shape of the single nanoparticles;

FIGS. 7a, 7b and 7c show respectively SEM image (7a) and EDX spectrum (7b and 7c) of enamel brushed with toothpaste contain Zn,Sr,FCHA according to the invention (in vitro test).

FIGS. 8a and 8b show respectively SEM image and EDX spectrum of enamel brushed with common toothpaste.

In the following Examples, percentages and parts are by weight unless otherwise indicated.

EXAMPLE 1

Comparative

Preparation of an Aqueous Suspension of Zn—CHA

An aqueous suspension of comparative zinc carbonate-substituted hydroxyapatite particles (Zn—CHA) was prepared according to the following method.

In a first step, 510 g of water was mixed with 50 g $CaCO_3$, 20 g of $ZnCO_3$ and 168 g $Ca(OH)_2$.

During this step, the pH was maintained between 3 and 8, more preferably between 3 and 5.

The resulting aqueous suspension was maintained under agitation between 0.5 and 8 hours, more preferably between 1 and 4 hours.

During this step, the resulting suspension was brought between a temperature of 23° and 40° C., more preferably between 27° and 35° C.

Successively, 225 mL of acid solution (constituted by a mixture of 85 mL of $H_3PO_4$ at 75% and 140 mL of distilled water) was added at the aqueous suspension previously prepared. The time of addition was included between 30 minutes and 6 hours, more preferably between 1 and 4 hours.

After this step, the suspension was maintained under agitation between 1 and 12 hours, more preferably between 3 and 9 hours.

The final pH of suspension is maintained between 6 and 13, more preferably between 7 and 12.

The X-Ray diffraction pattern of comparative Zn—CHA is showed in FIG. 1.

EXAMPLE 2

Comparative

Preparation of an Aqueous Suspension of F—ZnCHA

An aqueous suspension of comparative zinc carbonate-substituted fluoro-hydroxyapatite particles (F—ZnCHA) was prepared according to the following method.

In a first step, 540 g of water was mixed with 50 g $CaCO_3$, 20 g of $ZnCO_3$, 7 g $Na_2FPO_4$, and 168 g $Ca(OH)_2$.

During this step, the pH was maintained between 3 and 8, more preferably between 3 and 5.

The resulting aqueous suspension was maintained under agitation between 0.5 and 8 hours, more preferably between 1 and 4 hours.

During this step, the resulting suspension was brought between a temperature of 23° and 40° C., more preferably between 27° and 35° C.

Successively, 225 mL of acid solution (constituted by a mixture of 85 mL of $H_3PO_4$ at 75% and 140 mL of distilled water) was added at the aqueous suspension previously prepared. The time of addition-was included between 30 minutes and 6 hours, more preferably between 1 and 4 hours.

After this step, the suspension was maintained under agitation between 1 and 12 hours, more preferably between 3 and 9 hours.

The final pH of suspension is maintained between 6 and 13, more preferably between 7 and 12.

The X-Ray diffraction pattern of comparative F—ZnCHA is showed in FIG. 2.

EXAMPLE 3

Comparative

Preparation of an Aqueous Suspension of Sr—ZnCHA

An aqueous suspension of comparative zinc, strontium carbonate-substituted hydroxyapatite particles (Sr—ZnCHA) was prepared according to the following method.

In a first step, 540 g of water was mixed with 50 g $CaCO_3$, 20 g of $ZnCO_3$, 5 g $SrCO_3$, and 168 g $Ca(OH)_2$.

During this step, the pH was maintained between 3 and 8, more preferably between 3 and 5.

The resulting aqueous suspension was maintained under agitation between 0.5 and 8 hours, more preferably between 1 and 4 hours.

During this step, the resulting suspension was brought between a temperature of 23° and 40° C., more preferably between 27° and 35° C.

Successively, 225 mL of acid solution (constituted by a mixture of 85 mL of $H_3PO_4$ at 75% and 140 mL of distilled water) was added at the aqueous suspension previously prepared. The time of addition was included between 30 minutes and 6 hours, more preferably between 1 and 4 hours.

After this step, the suspension was maintained under agitation between 1 and 12 hours, more preferably between 3 and 9 hours.

The final pH of suspension is maintained between 6 and 13, more preferably between 7 and 12.

The X-Ray diffraction pattern of comparative Sr—Zn-CHA is showed in FIG. 3.

EXAMPLE 4

Preparation of an Aqueous Suspension of Particles According to the Invention

An aqueous suspension of carbonate-substituted fluoro-hydroxyapatite particles according to the invention with a solid residue comprised between 20% by weight and 40% by weight, more preferably between 25% by weight and 35% by weight, was prepared according to the following method.

In a first step, 550 g of water was mixed with 60 g $CaCO_3$, 20 g of $ZnCO_3$, 7 g of $Na_2FPO_4$, 5 g of $SrCO_3$ and 168 g $Ca(OH)_2$.

During this step, the pH was maintained between 3 and 8, more preferably between 3 and 5.

The resulting aqueous suspension was maintained under agitation between 0.5 and 8 hours, more preferably between 1 and 4 hours.

During this step, the resulting suspension was brought between a temperature of 23° and 40° C., more preferably between 27° and 35° C.

Successively, 250 mL of acid solution (constituted by a mixture of 150 mL of $H_3PO_4$ at 75% and 100 mL of distilled water) was added at the aqueous suspension previously prepared. The time of addition was included between 30 minutes and 6 hours, more preferably between 1 and 4 hours.

After this step, the suspension was maintained under agitation between 1 and 12 hours, more preferably between 3 and 9 hours.

The final pH of suspension is maintained between 6 and 13, more preferably between 7 and 12.

The suspension of particles was readily useable as such or as an active ingredient for the subsequent preparation of a dental care product according to the invention.

With reference to FIG. 4, the presence of both fluoride and strontium into substituted hydroxyapatite is important for their synergic effect on the degree of crystallinity. In fact, the crystallinity increase of Zn,Sr,FCHA (+8%) is advantageously greater than the sum of the single increase of crystallinity due to the presence, into the hydroxyapatite structure, of only fluoride ions (+3%) or only strontium ions (+1%).

EXAMPLE 5

Preparation of an Aqueous Suspension of Particles According to the Invention

An aqueous suspension of carbonate-substituted fluoro-hydroxyapatite particles according to the invention with a solid residue comprised between 20% by weight and 40% by weight, more preferably between 23% by weight and 33% by weight, was prepared according to the following method.

In a first step, 750 g of water was mixed with 55 g $CaCO_3$, 10 g of $ZnCO_3$, 5 g of $K_2CO_3$, 4 g of $Na_2CO_3$, 7 g of $SrCO_3$ and 155 g $Ca(OH)_2$.

During this step, the pH was maintained between 3 and 8, more preferably between 3 and 6.

The resulting aqueous suspension was maintained under agitation between 1 and 7 hours, more preferably between 2 and 4 hours.

During this step, the resulting suspension was brought between a temperature of 18° and 40° C., more preferably between 20° and 30° C.

Successively, 300 mL of acid solution (constituted by a mixture of 150 mL of $H_3PO_4$ at 75%, 20 mL of HF at 40% and 130 mL of distilled water) was added at the aqueous suspension previously prepared. The time of addition was included between 1 and 6 hours, more preferably between 2 and 4 hours.

After this step, the suspension was maintained under agitation between 1 and 12 hours, more preferably between 3 and 7 hours.

The final pH of suspension is maintained between 5 and 13, more preferably between 8 and 12.

The suspension of particles was readily useable as such or as an active ingredient for the subsequent preparation of a dental care product according to the invention.

EXAMPLE 6

Preparation of an Aqueous Suspension of Particles According to the Invention

An aqueous suspension of carbonate-substituted fluoro-hydroxyapatite particles according to the invention with a solid residue comprised between 20% by weight and 40% by weight, more preferably between 23% by weight and 33% by weight, was prepared according to the following method.

In a first step, 600 g of water was mixed with 50 g $CaCO_3$, 15 g of $ZnCO_3$, 10 g of $K_2CO_3$, 6 g of $Na_2CO_3$, 10 g of $SrCO_3$ and 170 g $Ca(OH)_2$.

During this step, the pH was maintained between 3 and 9, more preferably between 4 and 7.

The resulting aqueous suspension was maintained under agitation between 30 minutes and 7 hours, more preferably between 1 and 3 hours.

During this step, the resulting suspension was brought between a temperature of 15° and 40° C., more preferably between 20° and 25° C.

Successively, 300 mL of acid solution (constituted by a mixture of 160 mL of $H_3PO_4$ at 75%, 10 mL of HF at 40% and 130 mL of distilled water) was added at the aqueous suspension previously prepared. The time of addition was included between 1 and 8 hours, more preferably between 1.5 and 4 hours.

After this step, the suspension was maintained under agitation between 2 and 12 hours, more preferably between 6 and 9 hours.

The final pH of suspension is maintained between 5 and 13, more preferably between 8 and 13.

The suspension of particles was readily useable as such or as an active ingredient for the subsequent preparation of a dental care product according to the invention.

EXAMPLE 7

Toothpaste

A toothpaste including carbonate-substituted fluoro-hydroxyapatite particles according to the invention was prepared according to the following method and from the following ingredients.

In a first step, an aqueous suspension including carbonate-substituted fluoro-hydroxyapatite particles (Zn,Sr,FCHA) (total solid content: 30% by weight) was prepared in the same manner and using the same ingredients and quantities described in Example 4.

The aqueous suspension thus obtained, was then mixed with the other ingredients of the toothpaste as shown in the table below except for the surfactant.

The mixing was carried out in a conventional mixing apparatus maintained under a suitable vacuum degree selected among the usual values known to those skilled in the art.

Once a homogeneous mixture was obtained, the surfactant was incorporated in the mixing apparatus while maintaining a predetermined vacuum degree selected among the usual values known to those skilled in the art.

In this way, a toothpaste was obtained having the composition reported in the following Table 1.

TABLE 1

| Ingredient | Amount [%] |
|---|---|
| Sodium carboxymethylcellulose | 1.0 |
| Zn, Sr, FCHA particles | 15.0 |
| Sorbitol syrup | 15.0 |
| Glycerine | 15.0 |
| Sodium saccharine | 0.25 |
| Hydroglycolic moss extract titrated in 2% usnic acid | 0.5 |
| Thickening silica | 1.0 |
| Abrasive silica | 18.0 |
| Tetrapotassium pyrophosphate | 3.0 |
| Titanium dioxide | 0.9 |
| Sodium lauryl sulfate | 0.5 |
| Mint flavor | 1.3 |
| Citric acid | 0.25 |
| Water | balance |

EXAMPLE 8

Evaluation of the Coating Formation on the Surface of the Enamel In Vitro

Slabs of enamel (3×3 mm) were obtained from interproximal surfaces of premolars extracted for orthodontic reasons. After the extraction, the teeth were cut with diamond disks and the slabs obtained were sonicated for 10 min in 50% by weight of ethanol in order to removed any debris. The slabs were etched with 37% by weight of orthophosphoric acid for 1 min, then repeatedly washed with distilled water using an electric toothbrush and air dried. The test was then carried out by treating various slabs of enamel with a common toothpaste and an toothpaste containing 10% wt of the active agent Zn,Sr,FCHA object of the present invention.

There have been five tests in parallel for greater repetition of the experiment and better statistical data.

The protocol used was as follows:

Each enamel slab was brushed three times a day for a period of 21 days. The intervals between brushing sessions were more than 5 hours. Any washing process has been performed for 30 sec using an electric toothbrush submitted at constant pressure and using a bean sized aliquot of toothpaste wetted with tap water, closely resembling the in vivo usual tooth-brushing procedure. After every treatment, the single enamel slab was washed with tap water using a cleaned tooth-brush in order to remove residual tooth-paste. Toothbrushes were repeatedly washed with tap water after every utilization.

After the brushing treatment 21 days long each enamel slab have been characterized by X-Ray diffraction technique (DRX), Scanning Electro microscopy (SEM) with EDX probe and Infrared Fourier Transformed Spectroscopy (FTIR).

The analysis made by SEM-EDX probe, shows that the enamel surfaces treated with common toothpaste have a Ca/P molar ratio of 1.9 (FIGS. 8a and 8b). The Ca/P molar ratio of 1.9 is the characteristic value of natural enamel.

EDX analysis performed on the enamel brushed with toothpaste containing Zn,Sr,FCHA according to the invention, shows that the surface of the enamel has a ratio of Ca/P of 1.5-1.7 which is the same as that of the Zn,Sr,FCHA microcrystals contained in the toothpaste.

This therefore means that on the surface of the enamel a two-layer coating is formed (FIGS. 7a, 7b and 7c). FIG. 7a shows an overlapping of two coatings by showing a ratio of Ca/P of 1.5-1.7:

a first inner coating of reduced thickness on the surface of the enamel formed by a layer of the Zn,Sr,FCHA microcrystals (FIG. 7c) and a second discontinuous outer coating on the first inner coating of Zn,Sr,FCHA microcrystals (FIG. 7b).

In FIG. 7a uncovered areas of the first inner coating are visible due to the discontinuity in the outer coating.

Advantageously, in the enamel treated with toothpaste containing Zn,Sr,FCHA according to the invention, it was observed the formation of a two-layer coating with a variable thickness comprised between 10 μm and 20 μm on the outer surface of the enamel, even in the limited time available during the normal routine of dental hygiene.

EXAMPLE 9

Mouthwash

A mouthwash including Zn,Sr,FCHA particles according to the invention was prepared by mixing a suspension produced in accordance with the preceding Example 4 in a conventional way with conventional ingredients.

A mouthwash was obtained having the composition reported in the following Table 2.

TABLE 2

| Ingredient | Amount [%] |
|---|---|
| Zn, Sr, FCHA particles | 5 |
| Sorbitol syrup | 3 |
| Glycerine | 3 |
| Sodium saccharine | 0.25 |
| Hydroglycolic moss extract titrated in 2% usnic acid | 0.5 |
| Tetrapotassium pyrophosphate | 1 |
| Sodium lauryl sulfate | 0.2 |
| Mint flavor | 0.5 |
| Citric acid | 0.1 |
| Water | balance |

EXAMPLE 10

Chewing Gum for Tooth Cleaning

A chewing gum including Zn,Sr,FCHA particles according to the invention was prepared by mixing a suspension produced in accordance with the preceding Example 4 in a conventional way with conventional ingredients.

A chewing gum was obtained having the composition reported in the following Table 3.

TABLE 3

| Ingredient | Amount [%] |
| --- | --- |
| Chewing gum base | 91.65 |
| Zn, Sr, FCHA particles | 4 |
| Glycerine | 3 |
| Sodium saccharine | 0.025 |
| Hydroglycolic moss extract titrated in 2% usnic acid | 0.1 |
| Mint flavor | 1 |

Tests conducted on volunteers who used a dental care product of the present invention, during the normal routine of dental hygiene, showed the formation of a thin biomimetic coating on the enamel surface which is resistant for about 24 hours after usual tooth-brushing procedure.

The invention claimed is:

1. A dental care product comprising carbonate-substituted fluoro-hydroxyapatite particles having the formula:

$$Ca_{(10-x-y-m)}Zn_xSr_yM_m(PO_4)_{(6-z)}(CO_3)_z(OH)_{2-w}F_w$$

wherein M is selected from the group consisting of Mg, Se, K and mixtures thereof; x is a number between 0 and 0.02; y is a number between 0.0010 and 0.015; m is a number between 0 and 0.5; z is a number between 0.0010 and 0.010 and w is a number between 0.000002 and 0.0001; and
wherein said fluoro-hydroxyapatite particles have a crystallinity degree (CD) between 50 and 85%.

2. A product according to claim 1, wherein M is Mg, x, y, z and w are as defined in claim 1 and m is a number between 0.01 and 0.5; and
wherein said fluoro-hydroxyapatite particles have a crystallinity degree (CD) comprised between 55 and 80%.

3. A product according to claim 1, wherein M is $Mg_{m1}Se_{m2}$ wherein $m_1$ is a number between 0.01 and 0.5, $m_2$ is a number between 0.001 and 0.5 and $m_1+m_2 \leq 0.5$, x, y, z and w are as defined in claim 1; and
wherein said fluoro-hydroxyapatite particles have a crystallinity degree CD comprised between 60 and 75%.

4. A product according to claim 1, wherein M is $Mg_{m1}Se_{m2}K_{m3}$ wherein $m_1$ is a number between 0.01 and 0.5, $m_2$ is a number between 0.001 and 0.5, $m_3$ is a number between 0.0005 and 0.5 and $m_1+m_2+m_3 \leq 0.5$, x, y, z and w are as defined in claim 1; and
wherein said fluoro-hydroxyapatite particles have a crystallinity degree CD comprised between 60 and 80%.

5. A product according to claim 1, in the form of suspension, oil, gel or solid.

6. A product according to claim 5, in the form of a suspension including from 1% to 40% by weight of said particles.

7. A product according to claim 6, having a pH between 6 and 12.

8. A product according to claim 5, selected from the group consisting of: toothpaste, tooth powder, chewing gum for oral and dental hygiene, ointment for the gums and mouthwash.

9. Carbonate-substituted fluoro-hydroxyapatite particles having the formula:

$$Ca_{(10-x-y-m)}Zn_xSr_yM_m(PO_4)_{(6-z)}(CO_3)_z(OH)_{2-w}F_w$$

wherein M is selected from the group consisting of Mg, Se, K and mixtures thereof; x is a number between 0 and 0.02; v is a number between 0.0010 and 0.015; m is number between 0 and 0.05; z is a number between 0.0010 and 0.010; and w is a number between 0.000002 and 0.0001; and wherein said fluoro-hydroxyapatite particles have a crystallinity degree (CD) between 50 and 85%.

10. A process for manufacturing a dental care product selected from the group consisting of: toothpaste, tooth powder, chewing gum, ointment for the gums, and mouthwash comprising the steps of:
a) providing an aqueous suspension including particles according to claim 9; and
b) mixing said aqueous suspension with other ingredients of the dental care product.

11. A process for manufacturing a dental care product selected from the group consisting of: toothpaste, tooth powder, chewing gum, ointment for the gums, and mouthwash comprising the steps of:
a') providing solid particles according to claim 10; and
b') mixing the solid particles with other ingredients of the dental care product.

12. A process according to claim 10, wherein said step a) comprises the steps of:
$a_1$) preparing an aqueous solution or suspension comprising a Ca compound, Ca carbonate and optionally a F compound;
$b_1$) adding Sr and optionally Zn and/or a metal M compound selected from Mg, Se, K and mixtures thereof to the aqueous solution or suspension of step $a_1$);
$c_1$) preparing a mixture of phosphoric acid and optionally a F compound;
$d_1$) forming an aqueous suspension of solid particles of a carbonate-substituted fluoro-hydroxyapatite by adding said mixture to the aqueous solution or suspension of step $b_1$), provided that at least one F compound is present in the mixture of step $c_1$) and/or in the aqueous solution or suspension of step $b_1$), while simultaneously agitating the same over a time comprised between 30 minutes and 7 hours while maintaining said solution or suspension at a temperature comprised between 10 and 90° C.; and
$e_1$) agitating a suspension of particles obtained from step $d_1$) over a time comprised between 1 and 48 hours at a temperature comprised between 10° C. and 90° C.

13. A process according to claim 12, wherein the aqueous suspension obtained from step $d_1$) has a pH comprised between 5 and 13.

14. A process according to claim 12, wherein said Ca compound is a calcium salt selected from the group consisting of: calcium hydroxide, calcium carbonate, calcium acetate, calcium oxalate, calcium nitrate, and mixtures thereof.

15. A process according to claim 12, wherein said Zn compound is a zinc salt selected from the group consisting of: zinc carbonate, zinc oxide, and zinc hydroxide, zinc acetate, zinc nitrate, and mixtures thereof.

16. A process according to claim 12, wherein said F compound is a fluoride salt selected from the group consisting of: sodium fluoride, sodium fluoride phosphate, fluoridric acid, and mixtures thereof.

17. A process according to claim 12, wherein said Sr compound is a strontium salt selected from the group consisting of: strontium carbonate, strontium oxide, and strontium hydroxide, and mixtures thereof.

18. A process according to claim 12, wherein said M compound is a metal salt of a compound selected from the group consisting of Mg compound, Se compound, K compound and mixtures thereof.

19. A process according to claim 18, wherein said Mg compound is a magnesium salt selected from the group consisting of: magnesium carbonate, magnesium oxide, magnesium hydroxide, magnesium acetate, and mixtures thereof.

20. A process according to claim 18, wherein said Se compound is a selenium salt of a compound selected from the group consisting of: selenium dioxide, selenium trioxide, selenious acid, selenic acid, and mixtures thereof.

21. A process according to claim 18, wherein said K compound is a potassium salt selected from the group consisting of: potassium carbonate, potassium oxide, potassium hydroxide, potassium nitrate, potassium hydrogen carbonate, potassium acetate, and mixtures thereof.

22. A process according to claim 12, wherein step $c_1$) is carried out while bubbling air, a $CO_2$-containing gas or a mixture thereof through the aqueous solution or suspension of step $a_1$) and $b_1$).

23. A process according to claim 12, wherein step $c_1$) is carried out by adding an aqueous solution including $PO_4^{3-}$ and optionally $F^-$ ions to the aqueous solution or suspension of step $a_1$) and $b_1$).

24. A process according to claim 23, wherein said aqueous solution including $PO_4^{3-}$ and optionally $F^-$ ions further comprises $HCO_3^-$ ions.

25. A process according to claim 24, wherein said aqueous solution including $HCO_3^-$, $PO_4^{3-}$ and optionally $F^-$ ions is prepared by bubbling air, $CO_2$ or a mixture thereof through water to obtain a solution of carbonic acid and then adding $H_3PO_4$ and F compound thereto.

26. A process according to claim 23, wherein step $c_1$) is carried out by simultaneously adding a first solution including $CO_3^{2-}$ ions and a second solution containing $PO_4^{3-}$ and optionally $F^-$ ions to the aqueous solution or suspension of $a_1$) and $b_1$).

27. A process according to claim 11, wherein said step a') comprises the steps of:
   $a_2$) preparing an aqueous suspension of carbonate-substituted fluoro-hydroxyapatite solid particles by a process according to claim 12;
   $b_2$) separating the solid particles from the suspension obtained from step $a_2$);
   $c_2$) drying the wet solid particles thus obtained.

28. A process according to claim 27, wherein said separation step $b_2$) is carried out by decantation, centrifugation or filtration.

29. A process according to claim 27, wherein said drying step $c_2$) is carried out by freeze-drying the wet solid particles at a temperature lower than 0° C. until reaching a constant weight.

30. A process according to claim 27, further comprising the step of
   $d_2$) washing the separated solid particles with water or a basic solution prior to effecting said drying step $c_2$).

31. A process according to claim 10, wherein mixing step b) is carried out in a mixing apparatus maintained under vacuum.

32. A process according to claim 10, wherein mixing step b) is carried out by
   $b^1$) mixing the aqueous suspension of step a) with other ingredients of the dental care product except for any surfactant;
   $b^2$) incorporating at least one surfactant into the mixture thus obtained.

33. A method of providing at a tooth outer surface a source of $F^-$ and $Sr^{++}$ ions which are locally released at an acidic pH by hydroxyapatite carrier particles, the method comprising contacting the teeth with a dental care product according to claim 1 so as to form on the tooth outer surface a film including said carbonate-substituted fluoro-hydroxyapatite particles.

34. A process according to claim 11, wherein mixing step b') is carried out in a mixing apparatus maintained under vacuum.

\* \* \* \* \*